United States Patent
Ohishi et al.

(10) Patent No.: US 8,260,017 B2
(45) Date of Patent: Sep. 4, 2012

(54) ROTATION CENTER IDENTIFYING METHOD AND APPARATUS, RING ARTIFACT CORRECTION METHOD, AND X-RAY DIAGNOSTIC APPARATUS EMPLOYING THE SAME

(75) Inventors: Satoru Ohishi, Otawara (JP); Clay Christopher Smith, Buffalo Grove, IL (US)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 605 days.

(21) Appl. No.: 12/388,788

(22) Filed: Feb. 19, 2009

(65) Prior Publication Data

US 2010/0208969 A1 Aug. 19, 2010

(51) Int. Cl.
*G06K 9/00* (2006.01)

(52) U.S. Cl. .............. 382/128; 382/131; 378/4; 378/15; 378/901

(58) Field of Classification Search .................. 382/128, 382/131; 378/4, 15, 901
See application file for complete search history.

(56) References Cited

U.S. PATENT DOCUMENTS

| 4,670,840 | A | * | 6/1987 | Freundlich | 378/7 |
| 5,825,841 | A | * | 10/1998 | Timmer | 378/4 |
| 6,819,734 | B2 | * | 11/2004 | Raupach | 378/4 |
| 2008/0019607 | A1 | * | 1/2008 | Star-Lack et al. | 382/264 |

* cited by examiner

*Primary Examiner* — Francis M Legasse, Jr.
(74) *Attorney, Agent, or Firm* — Oblon, Spivak, McClelland, Maier & Neustadt, L.L.P.

(57) ABSTRACT

The influences of the vibrations and the like of a rotational radiography system are corrected with respect to a projection image for each projection direction which contains an artificial artifact, and volume data containing only a ring artifact is generated by image reconstruction using the projection images. A ring center is determined by using this volume data, and polar coordinate conversion of an actual radiographed image is executed by using the ring center as an origin, thereby extracting a signal (ring artifact) parallel to an angular axis.

28 Claims, 9 Drawing Sheets

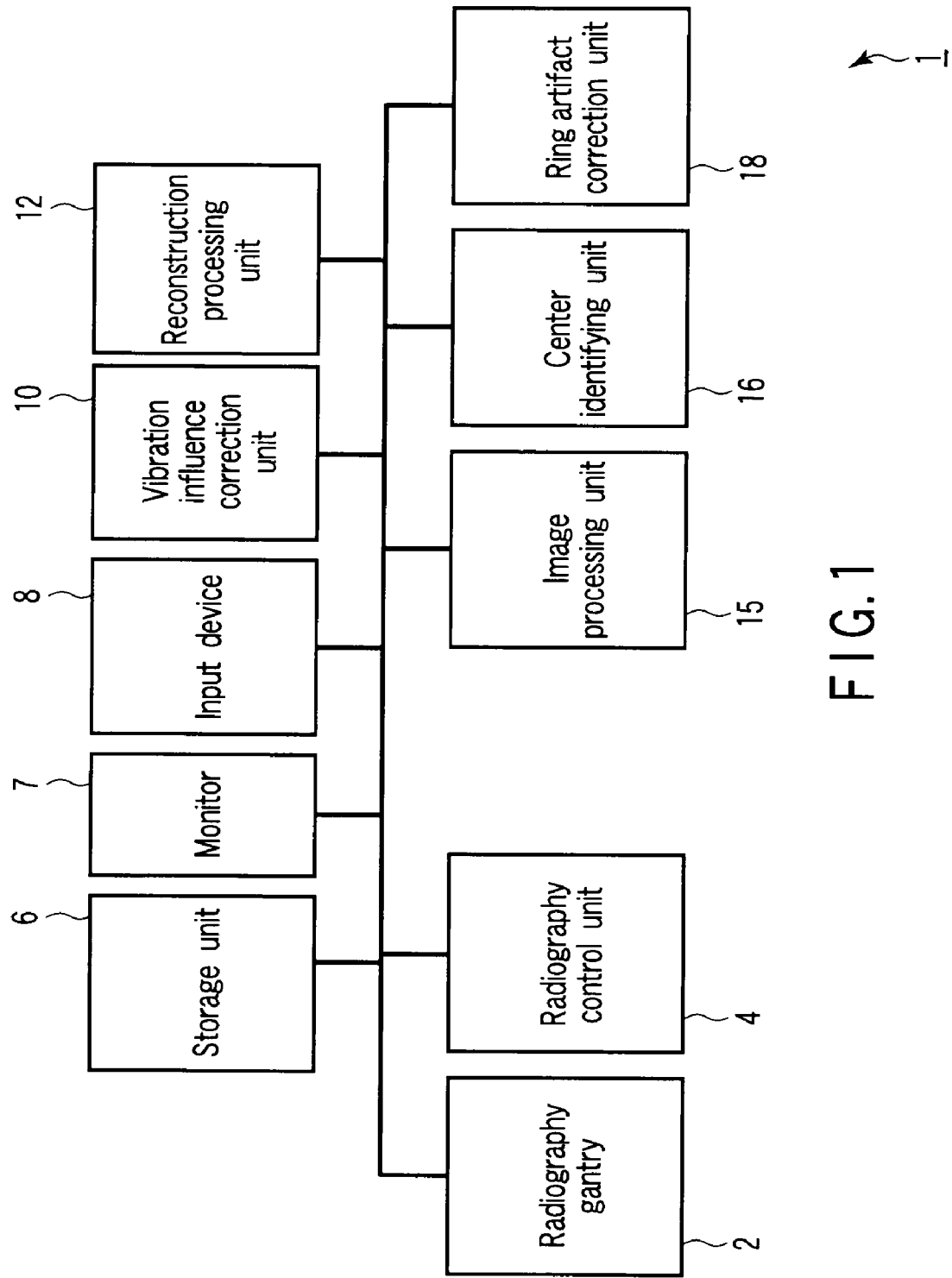
F I G. 1

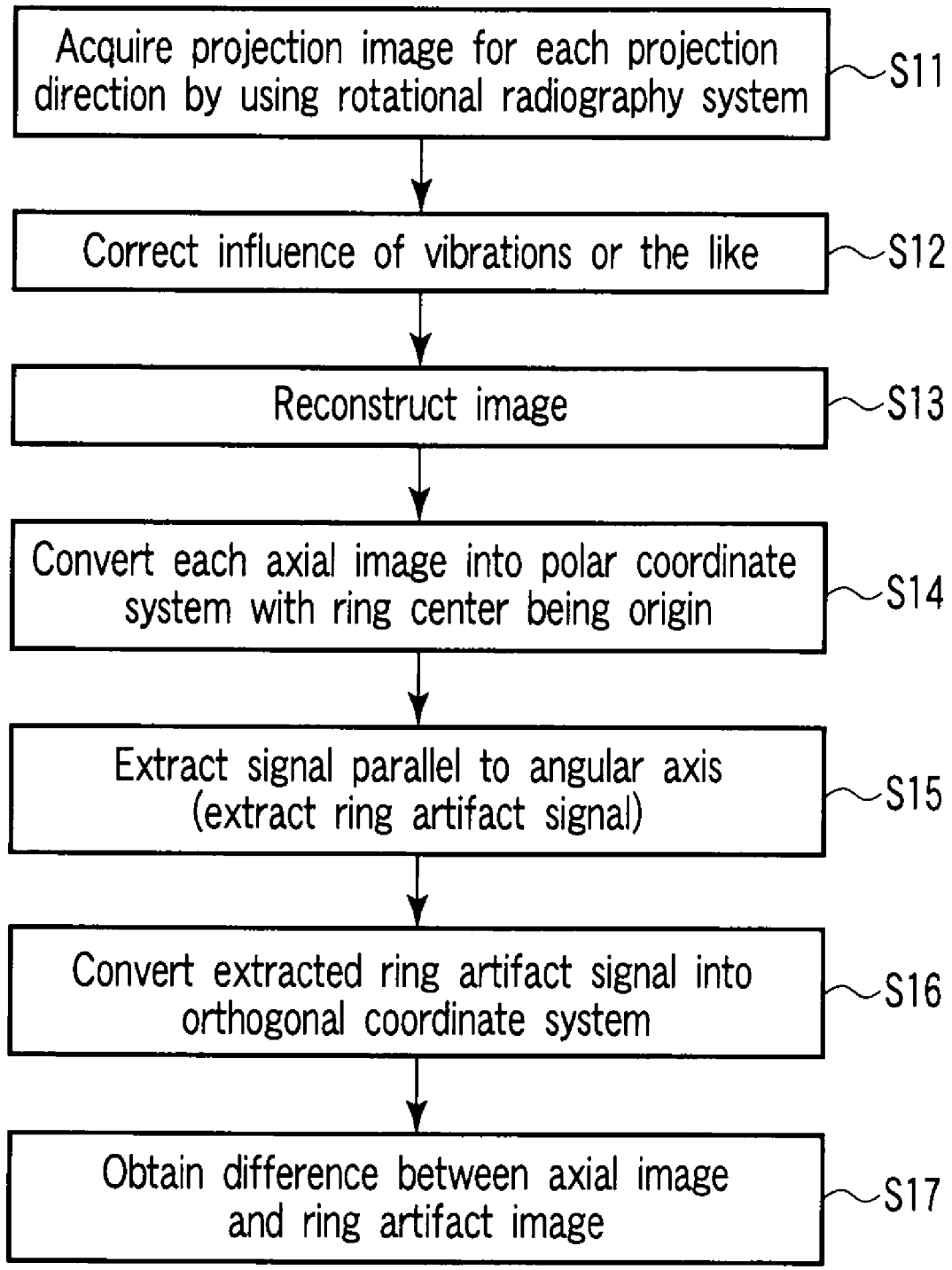
F I G. 6

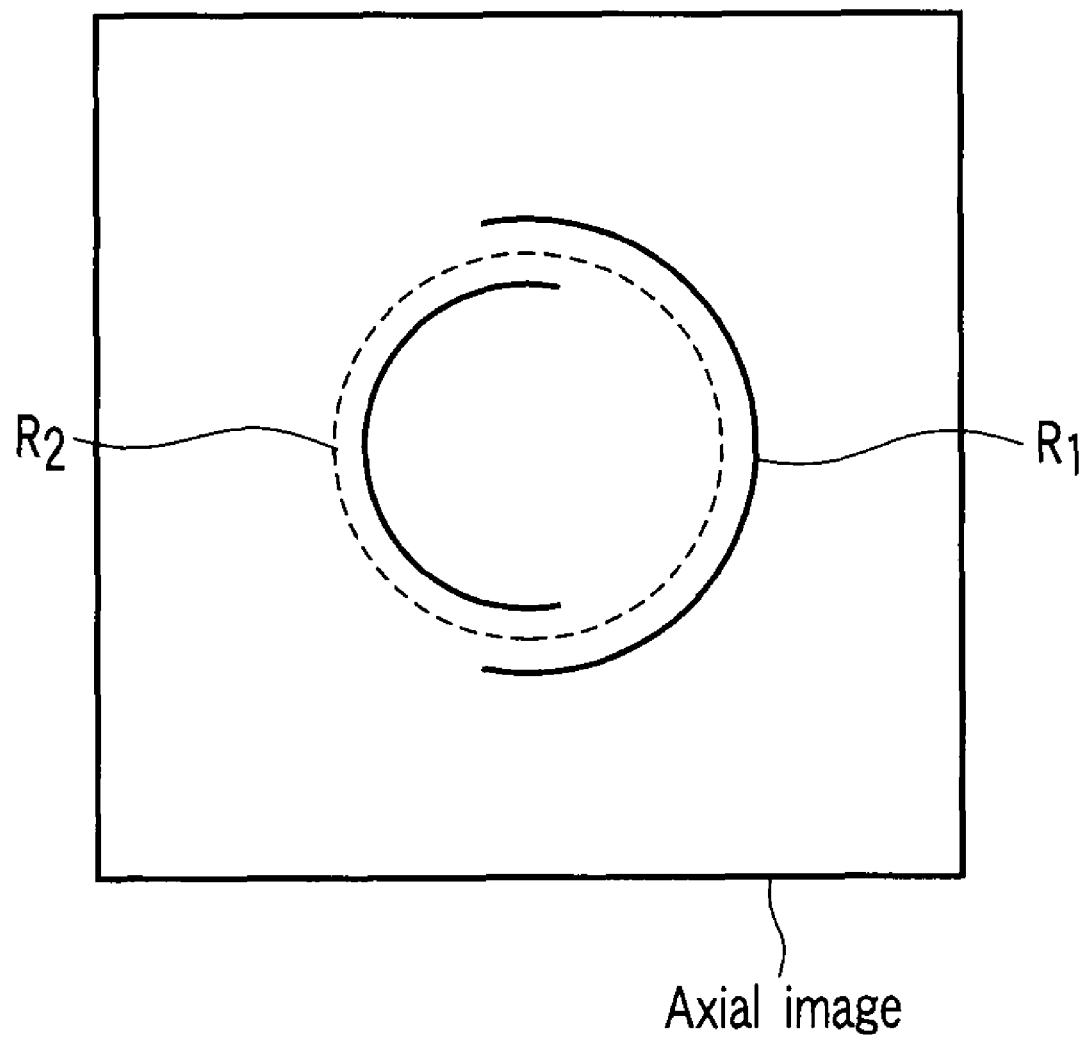
F I G. 10

ROTATION CENTER IDENTIFYING METHOD AND APPARATUS, RING ARTIFACT CORRECTION METHOD, AND X-RAY DIAGNOSTIC APPARATUS EMPLOYING THE SAME

BACKGROUND OF THE INVENTION

1. Field of the Invention

The present invention relates to a technique for more accurately determining a ring center in a case wherein correction (ring artifact correction) is performed to remove, for example, a concentric artifact (ring artifact) occurring in an image captured by using an X-ray diagnostic apparatus.

2. Description of the Related Art

A ring artifact is well known in the field of X-ray computed tomographic apparatuses, and is said to occur due to a small sensitivity error of a detector element. This artifact is very low in density but poses a problem especially when soft tissue or the like is to be observed.

Recently, there has been an increasing need to three-dimensionally image soft tissue and observe the resultant image by using an X-ray diagnostic apparatus including a two-dimensional detector. Such three-dimensional imaging is generally performed by using a system comprising a rotating gantry such as an almost C-shaped arm instead of a rigid rotating gantry like that of an X-ray computed tomographic apparatus. Such a system executes radiography for X-ray images upon stopping the almost C-shaped arm (rotational radiography system), on which an X-ray generating unit and an X-ray detecting unit are mounted, at a desired position by, for example, translating and rotating the C-shaped arm. For this reason, a mechanical system comprising the support portion, driving portion, and the like of the almost C-shaped arm suffers from vibrations or deflection accompanying movement or stoppage, backlash due to long-time use, the movement of the center of gravity after rotation through a given angle or more, and the like. Such variations and the like cause wobbling of the almost C-shaped arm around its rotation center, thus causing a deterioration in image quality.

In order to solve this problem, a conventional X-ray diagnostic apparatus radiographs a phantom of a known structure, derives the relative positional relationship between the phantom and an obtained projection image, and corrects the influences of vibrations and the like on the image by using the relationship.

When ring artifact correction is to be performed, it is necessary to identify the position of the center of a ring artifact (ring center) on an image. This ring center corresponds to the rotation center of a rotational radiography system. A conventional X-ray diagnostic apparatus having an almost C-shaped arm defines the system of the reconstruction coordinates with reference to a phantom center used for the acquisition of correction data for removing the influences of vibrations and the like. Consequently the position of the ring center depends on the position of the phantom.

In the conventional X-ray diagnostic apparatus, since the positions of the rotation center (that is the position of the ring center) is identified by manual operation on reconstruction images, a problem arises in terms of accuracy. In addition, every time correction data for removing the influences of vibrations and the like is updated, it is necessary to identify the position of a ring center. This operation is very cumbersome and is not practical.

BRIEF SUMMARY OF THE INVENTION

The present invention has been made in consideration of the above situation, and has as its object to provide a rotation center identifying method, a ring artifact correction method, a rotation center identifying apparatus, an x-ray diagnostic apparatus, a recording medium on which a program for executing rotation center identification is recorded, and a recording medium on which a program for executing ring artifact correction recorded, which can identify a rotation center and perform ring artifact correction more easily and accurately than the prior art.

According to an aspect of the present invention, it is provided that an identifying method of a central position of rotation of a rotational imaging system of an imaging apparatus which executes imaging while rotating, the method comprises: executing, by using a projection image for each projection direction which contains an artificial artifact, correction for removing an influence of a spatial positional shift due to a mechanical factor and reconstruction of volume data containing a ring artifact due to the artificial artifact; and identifying a ring center of the ring artifact as a position of a rotation center of the rotational imaging system by using the volume data.

According to another aspect of the present invention, it is provided that a ring artifact correction method comprises: executing, by using a projection image for each projection direction which contains an artificial artifact, correction for removing an influence of a spatial positional shift due to a mechanical factor and reconstruction of volume data containing a ring artifact due to the artificial artifact; and identifying a ring center of the ring artifact as a position of a rotation center of the rotational imaging system by using the volume data; correcting, using the ring center, a ring artifact occurring in a projection image acquired by using rotational imaging system for each projection direction.

According to yet another aspect of the present invention, it is provided that an apparatus for identifying a central position of rotation of a rotational imaging system of an imaging apparatus which executes imaging while rotating, the apparatus comprises: a data processing unit which executes, by using a projection image for each projection direction which contains an artificial artifact, correction for removing an influence of a spatial positional shift due to a mechanical factor and reconstruction of volume data containing a ring artifact due to the artificial artifact; and an identifying unit which identifies a ring center of the ring artifact as a position of a rotation center of the rotational imaging system by using the volume data.

According to yet another aspect of the present invention, it is provided that an X-ray diagnostic apparatus comprises: a data processing unit which executes, by using a projection image for each projection direction which contains an artificial artifact, correction for removing an influence of a spatial positional shift due to a mechanical factor and reconstruction of volume data containing a ring artifact due to the artificial artifact; an identifying unit which identifies a ring center of the ring artifact as a position of a rotation center of the rotational imaging system by using the volume data; and a correction unit, using the ring center, a ring artifact occurring in a projection image acquired by using rotational imaging system for each projection direction.

According to yet another aspect of the present invention, it is provided that a recording medium configured to record program instruction for identifying method of a central position of rotation of a rotational imaging system of an imaging apparatus which executes imaging while rotating on a computer system enabling the computer system to perform: executing, by using a projection image for each projection direction which contains an artificial artifact, correction for removing an influence of a spatial positional shift due to a mechanical factor and reconstruction of volume data containing a ring artifact due to the artificial artifact; and identifying a ring center of the ring artifact as a position of a rotation center of the rotational imaging system by using the volume data.

According to yet another aspect of the present invention, it is provided that a recording medium configured to record program instruction for executing ring artifact correction on a computer system enabling the computer system to perform: executing, by using a projection image for each projection direction which contains an artificial artifact, correction for removing an influence of a spatial positional shift due to a mechanical factor and reconstruction of volume data containing a ring artifact due to the artificial artifact; and identifying a ring center of the ring artifact as a position of a rotation center of the rotational imaging system by using the volume data; correcting, using the ring center, a ring artifact occurring in a projection image acquired by using rotational imaging system for each projection direction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing an example of the arrangement of an X-ray diagnostic apparatus according to this embodiment;

FIG. 6 is a flowchart showing ring artifact correction processing;

FIG. 10 is examples of ring artifact included an artifact projection image in which an artificial artifact is produced;

DETAILED DESCRIPTION OF THE INVENTION

Figure 2:
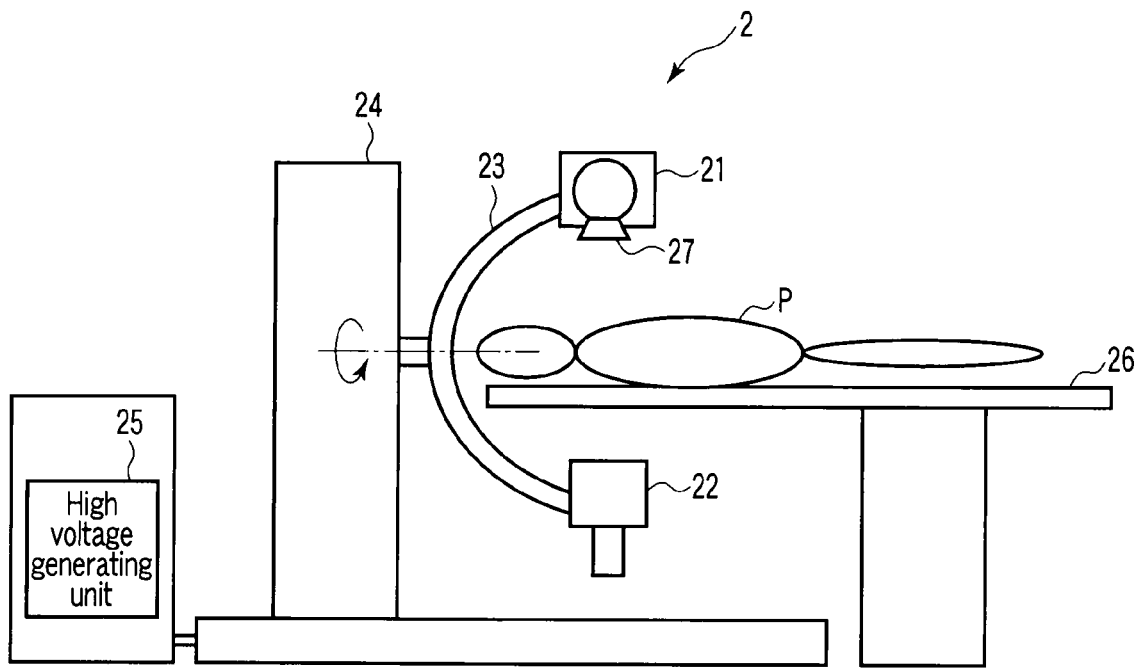
FIG. 2 is a view showing an example of the outer appearance of a radiography gantry 6.

An embodiment of the present invention will be described below with reference to the views of the accompanying drawing. Note that in the following description, the same reference numerals denote constituent elements having almost the same functions and arrangements, and a repetitive description will be made only when required. The technical idea of the present invention can be applied to an image diagnostic apparatus which acquires images while rotating a radiography system around a given rotation axis. For the sake of concrete description, this embodiment will exemplify an X-ray diagnostic apparatus which captures an X-ray image upon stopping an almost C-shaped arm, on which an X-ray generating unit and an X-ray detecting unit are mounted, at a desired position by, for example, translating and rotating the arm.

FIG. 1 shows the arrangement of an X-ray diagnostic apparatus 1 according to this embodiment. The X-ray diagnostic apparatus 1 comprises a radiography gantry 2, radiography control unit 4, storage unit 6, monitor 7, input device 8, vibration influence correction unit 10, reconstruction processing unit 12, image processing unit 15, center identifying unit 16, and ring artifact correction unit 18.

FIG. 2 shows an example of the outer appearance of the radiography gantry 2. As shown in FIG. 2, the radiography gantry 2 includes an X-ray tube 21, X-ray detector 22, C-arm 23, stand 24, high voltage generating unit 25, bed 26, and X-ray stop device 27.

The high voltage generating unit 25 generates a high voltage to be applied between the electrodes of the X-ray tube 21, and also generates a filament current to be supplied to the cathode filament of the X-ray tube 21. Upon receiving the high voltage and filament current, the X-ray tube 21 generates X-rays. The X-ray stop device 27 shapes X-rays generated by the X-ray tube 21. The X-ray detector 22 is typically a solid flat panel detector comprising a two-dimensional array of a plurality of detection elements (pixels) which directly or indirectly convert incident X-rays into electric charges. The X-ray tube 21 is mounted on, for example, one end of the floor type C-arm 23. The X-ray detector 22 is mounted on the other end of the C-arm 23. The X-ray detector 22 faces the X-ray tube 21 through a subject P placed on the bed 26. The C-arm 23 is rotatably supported on the stand 24. Repeating radiography while rotating the C-arm 23 makes it possible to acquire X-ray images (projection images) in many directions which are required for three dimensional image reconstruction.

The radiography control unit 4 controls the rotation of the C-arm 23, the application of high voltages from the high voltage generating unit 25 to the X-ray tube 21 and reading of signals from the X-ray detector 22 in order to execute rotational radiography and generate X-ray image (projection image) data.

The storage unit 6 stores artifact projection image to be described later, projection images associated with a subject to be examined which are acquired by using the rotational radiography system, and the position data of the ring center for each position of section which is generated by using a ring center (rotation center) identifying function (to be described later). The storage unit 6 also stores data for vibration influence correction (to be described later) for each projection direction.

The monitor 7 is a display device such as a CRT, plasma display, or liquid crystal display which displays an X-ray diagnostic image or the like in a predetermined form in accordance with a signal received from the reconstruction processing unit 12 or the image processing unit 15.

The input device 8 includes a keyboard, various kinds of switches, a mouse, and the like and is used to input a radiography instruction, image selection instruction, and the like.

The vibration influence correction unit 10 executes correction (to be referred to as "vibration influence correction"

hereinafter) to remove the influences (e.g., the positional shift or the like of the rotation center) of vibrations, deflection, backlash, and the like of the mechanical system of the radiography gantry 2.

The reconstruction processing unit 12 reconstructs volume data from projection images (X-ray images) in a plurality of projection directions.

The image processing unit 15 executes predetermined image processing such as volume rendering processing and image difference processing as needed.

The center identifying unit 16 identifies, for each position of section, the position of a ring center and the position of a rotation center in radiography during rotation of the C-arm by using the volume data reconstructed by the image processing unit 15.

The ring artifact correction unit 18 performs ring artifact correction by using the ring center identified by the center identifying unit 16 and projection images in a plurality of projection directions which are associated with the subject.

(Ring Center Identifying Function)

This function generates an artificial artifact and generates volume data by reconstructing only a ring artifact from projection images of the artifact. The function obtains the position of the ring artifact center (ring center) for each axial section by using this volume data and identifies the ring center as the position of the rotation center in radiography in which the C-arm is rotated. Note that, the axial section is a section to a reconstruction image which is substantially perpendicular to the rotation axis.

Note that processing (ring center identification processing) based on this ring center identifying function is executed as calibration at the time of, for example, installation or maintenance of the X-ray diagnostic apparatus 1. In this embodiment, the X-ray diagnostic apparatus 1 executes this ring center identification processing. However, the embodiment is not limited to this, and may be configured to execute this ring center identification processing by using an apparatus independent of the X-ray diagnostic apparatus 1 and store the obtained result in the storage unit 6.

Figure 3:
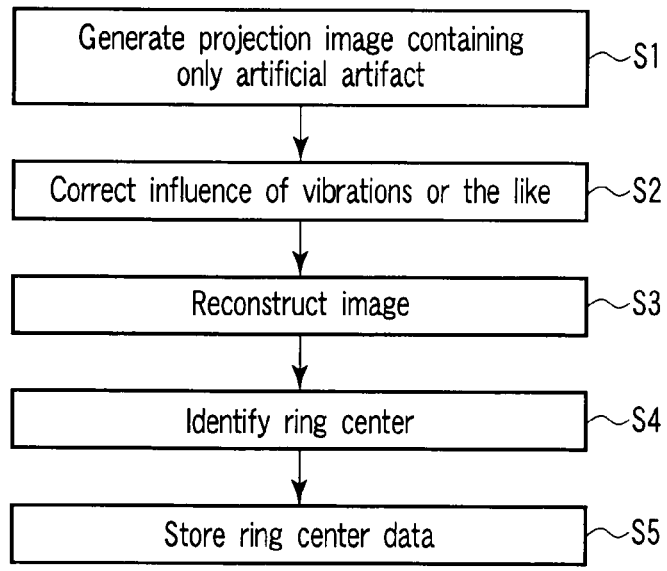
FIG. 3 is a flowchart showing ring center identification processing.

FIG. 3 is a flowchart showing a procedure for this ring center identification processing.

Figure 4:
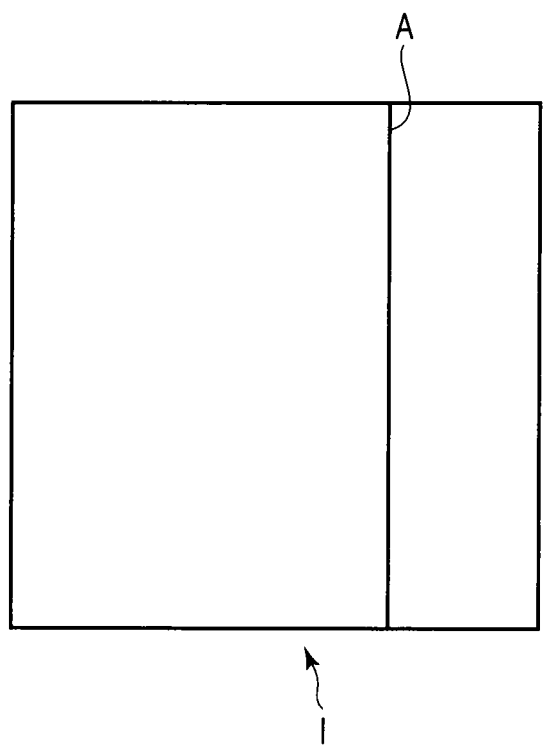
FIG. 4 is a view showing an example of a projection image (artifact projection image) including only an artificial artifact.

First of all, before this procedure, a projection image (artifact projection image) I containing only an artificial artifact A like that shown in FIG. 4 is generated for each projection direction in an amount corresponding to 210° (step S1). This artifact projection image is, for example, a virtual projection image. The storage unit 6 stores the generated artifact projection image.

Note that an example of the artificial artifact A shown in FIG. 4 is a line segment substantially parallel to the rotation axis of the C-arm 23. This artifact is used to cause a ring artifact on the entire volume data obtained by image reconstruction processing to be described later. This is a preferred embodiment of the present invention. However, the present invention is not limited to this. That is, the technical idea of the present invention is not limited to the shape and size of an artificial artifact. For example, an artificial artifact may be a region having a predetermined size, a line segment shorter than that shown in FIG. 4, a point, or the like.

The vibration influence correction unit 10 reads out an artifact projection image and vibration influence correction data for each projection direction from the storage unit 6, and performs correction processing for the removal of the influence of vibrations or the like for each artifact projection image (step S2). The reconstruction processing unit 12 generates volume data by executing image reconstruction processing by using the corrected artifact projection image for each projection direction (step S3).

Figure 5:
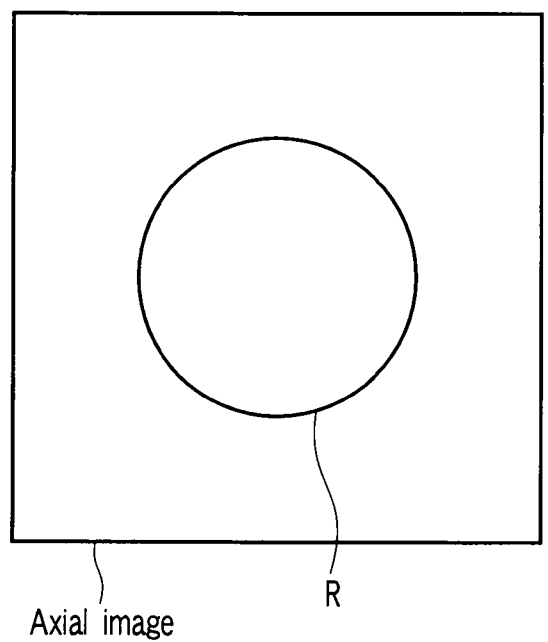
FIG. 5 is a view showing an example of a ring artifact on a reconstructed image due to the artificial artifact shown in FIG. 4.

The center identifying unit 16 identifies a ring center for each axial section by using the generated volume data (step S4). That is, the center identifying unit 16 generates an axial image for the each position of the section direction by using the generated volume data. Each axial image contains a ring artifact R like that shown in FIG. 5. The center identifying unit 16 identifies a ring center from the ring artifact contained in each axial image for each axial section by using a predetermined technique. The storage unit 6 stores the generated position data of the ring center for each axial section.

Instead of steps S2 and S3 described above, vibration-corrected reconstruction processing may be performed by use of the artifact projection image corresponding to each projection direction. The vibration-corrected reconstruction processing is intended to refer to reconstruction processing which includes vibration correction and which is performed in accordance with a calculation formula used for correcting a positional shift caused by vibration in each projection direction.

(Ring Artifact Correcting Function)

The ring artifact correcting function of the X-ray diagnostic apparatus 1 will be described next. This function performs ring artifact correction by using the ring center identified by ring center identification processing.

FIG. 6 is a flowchart showing a procedure for processing (ring artifact correction processing) based on this ring artifact correcting function.

First of all, the C-arm 23 continuously rotates about the body axis as a rotation axis under the control of the radiography control unit 4, and a plurality of projection images in different projection directions are acquired by repeatedly executing radiography for the subject P during this rotation (step S11). For example, the C-arm 23 rotates at a rate of 50°/sec for four sec, and about 200 frames of X-ray images are acquired during this period. The storage unit 6 stores the acquired projection images in association with the data of the respective projection directions.

The vibration influence correction unit 10 then reads out a projection image and vibration influence correction data for each projection direction from the storage unit 6, and performs correction processing to remove the influence of vibrations or the like with respect to each projection image (step S12). The reconstruction processing unit 12 reconstructs volume data by using the corrected projection image for each projection direction (step S13).

The ring artifact correction unit 18 generates an axial image for the each position of the section from the generated volume data, and converts the image coordinate system (the orthogonal coordinate system in this case) of each axial image into a polar coordinate system having the ring center identified in advance as an origin (step S14). Each axial image generated by the volume data has an orthogonal coordinate system. In this orthogonal coordinate system, a ring artifact concentrically exists as its name implies. Such a ring artifact exists as data parallel to an angular axis in the polar coordinate system.

The ring artifact correction unit 18 extracts data which exists substantially parallel to the angular axis in the polar coordinate system (step S15). The ring artifact correction unit 18 converts the extracted ring artifact into an orthogonal coordinate system to generate a ring artifact image (step S16). The ring artifact correction unit 18 removes the ring artifact from the volume data by subtracting the ring artifact image from the axial image (step S17).

(Modification 1)

It is preferable in terms of accuracy that an artificial artifact is located farthest from the center in a projection image. Note that artificial artifacts need not be identical to each other in all projection directions. For example, more accurate ring center identification can be performed by dividing the rotating region of the C-arm 23 into a plurality of small regions with reference to a predetermined position, and generating a plurality of types of artificial artifacts located at different positions or having different shapes in the respective small regions.

Note that each small region is determined on the basis of, for example, data associated with at least one of the barycentric position, vibration, deflection, and backlash of the rotational imaging system which is measured in advance for each projection direction. For a concrete description, assume that in this modification, the rotating region of the C-arm 23 is divided into right and left regions with reference to the rotation origin.

Figure 7:
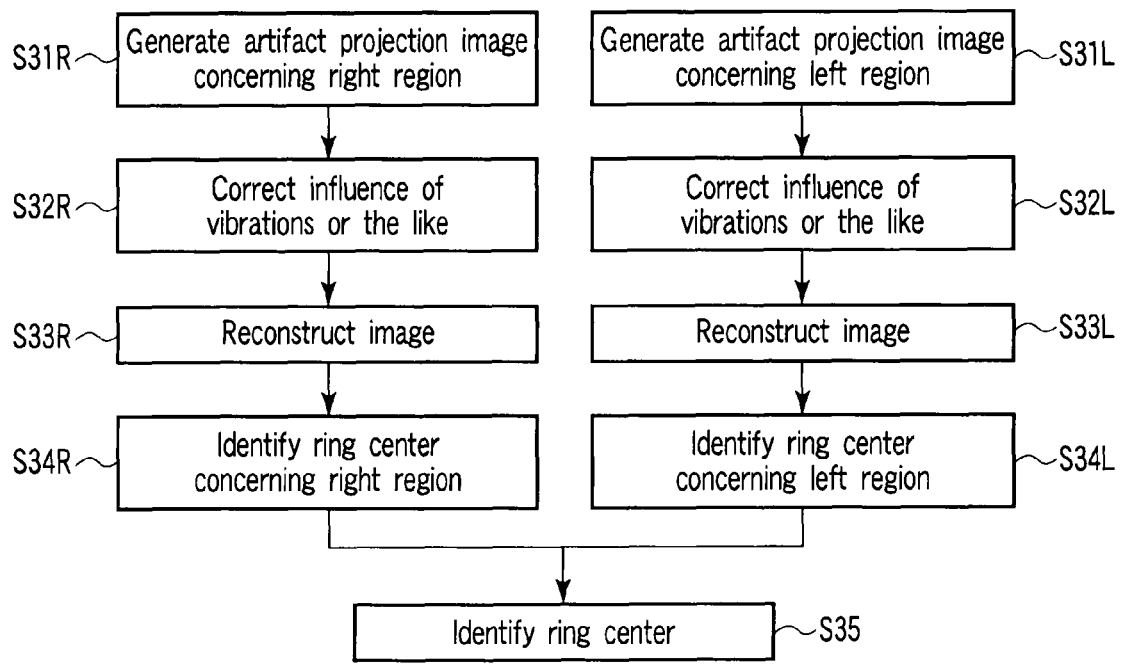
FIG. 7 is a flowchart showing a procedure for ring center identification processing according to the modification.

FIG. 7 is a flowchart showing a procedure for ring center identification processing according to the modification. As shown in FIG. 7, a center identifying unit 9 divides the rotating region of the C-arm 23 into right and left regions with reference to the rotation origin, and generates an artifact projection image in which an artificial artifact is produced on the right side of the image central position in the projection direction belonging to the right region (step S31R). The center identifying unit 9 then executes the same processing as that in steps S2 to S4 in FIG. 2 to identify the ring central position using the artifact reconstruction image belonging to the right region (steps S32R, S33R, and S34R).

Figure 8A:
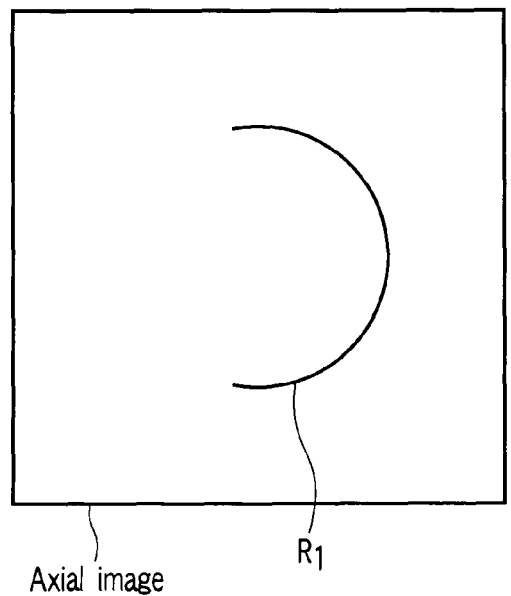
FIG. 8A.
Figure 8B:
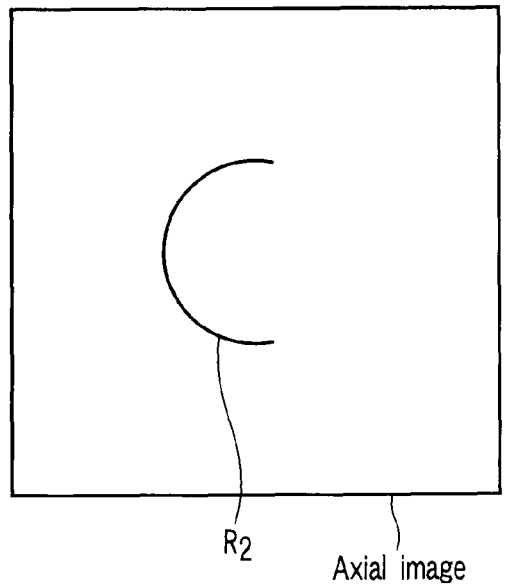
FIG. 8B are examples of ring artifact included an artifact projection image in which an artificial artifact is produced.

On the other hand, the center identifying unit 9 generates an artifact projection image in which an artificial artifact is produced on the left side of the image central position in the projection direction belonging to the left region (step S31L), and executes the same processing as that in steps S2 to S4 in FIG. 2 to identify the ring central position using the artifact reconstruction image belonging to the left region (steps S32L, S33L, and S34L). That is, the center identifying unit 9 generates an axial image for each section by using each generated volume data. The axial image generated from the volume image corresponding to the right region includes an arcuated ring artifact R1 like that shown in, for example, FIG. 8A. The axial image generated from the volume image corresponding to the left region includes an arcuated ring artifact R2 like that shown in, for example, FIG. 8B.

The center identifying unit 9 then identifies the ring center by using (e.g., averaging) the ring central position identified by using the artifact projection image belonging to the right region and the ring central position identified by using the artifact projection image belonging to the left region (step S35).

(Modification 2)

Figure 9:
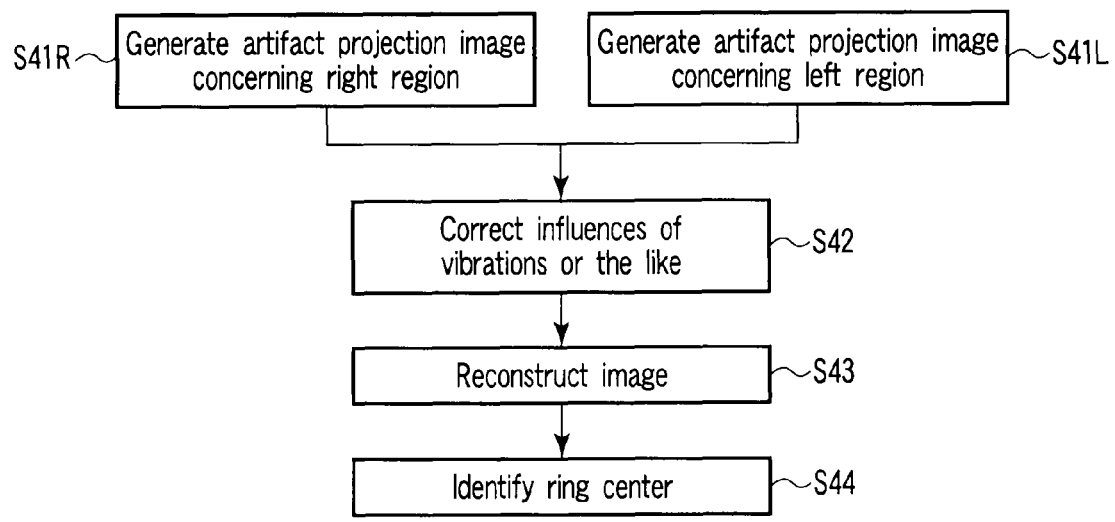
FIG. 9 is a flowchart showing a procedure for ring center identification processing according to another modification.

FIG. 9 is a flowchart showing a procedure for ring center identification processing according to another modification. Referring to FIG. 9, the center identifying unit 9 divides the rotating region of the C-arm 23 into right and left regions with reference to the rotation origin, and generates an artifact projection image in which an artificial artifact is produced on the right side of the image central position in the projection direction belonging to the right region (step S41R). On the other hand, the center identifying unit 9 generates an artifact projection image in which an artificial artifact is produced on the left side of the image central position in the projection direction belonging to the left region (step S41L). At this time, the artificial artifact is generated at a position where, for example, the distance from the image center differs from that on the right region so as to cause the ring artifacts on the volume data obtained by reconstruction processing to appear with different radii on the right and left regions (so as to prevent the ring artifacts corresponding to the right and left regions from overlapping).

The center identifying unit 9 then executes the same processing as that in steps S2 and S3 in FIG. 2 by using artifact projection images in all projection directions, which include the right and left regions, thereby generating volume data in which the ring artifacts corresponding to the right and left regions appear with different radii (steps S42 and S43).

Subsequently, the center identifying unit 9 identifies the ring center for each section by using the generated volume data (step S44). That is, the center identifying unit 9 generates an axial image for the each position of the section by using the generated volume data. Each axial image contains the ring artifacts R1 and R2 having different radii like those shown in, for example, FIG. 10. The center identifying unit 9 identifies the ring central position for each axial section from the ring artifacts R1 and R2 contained in the axial image by a predetermined technique (e.g., by dividing the ring artifacts R1 and R2 from the ring center by use of a radius, identifying the centers of the divisions of the artifacts R1 and R2 in a similar manner to that of S34R and S34L, and then averaging the central positions identified from the ring artifacts R1 and R2).

(Modification 3)

Figure 11:
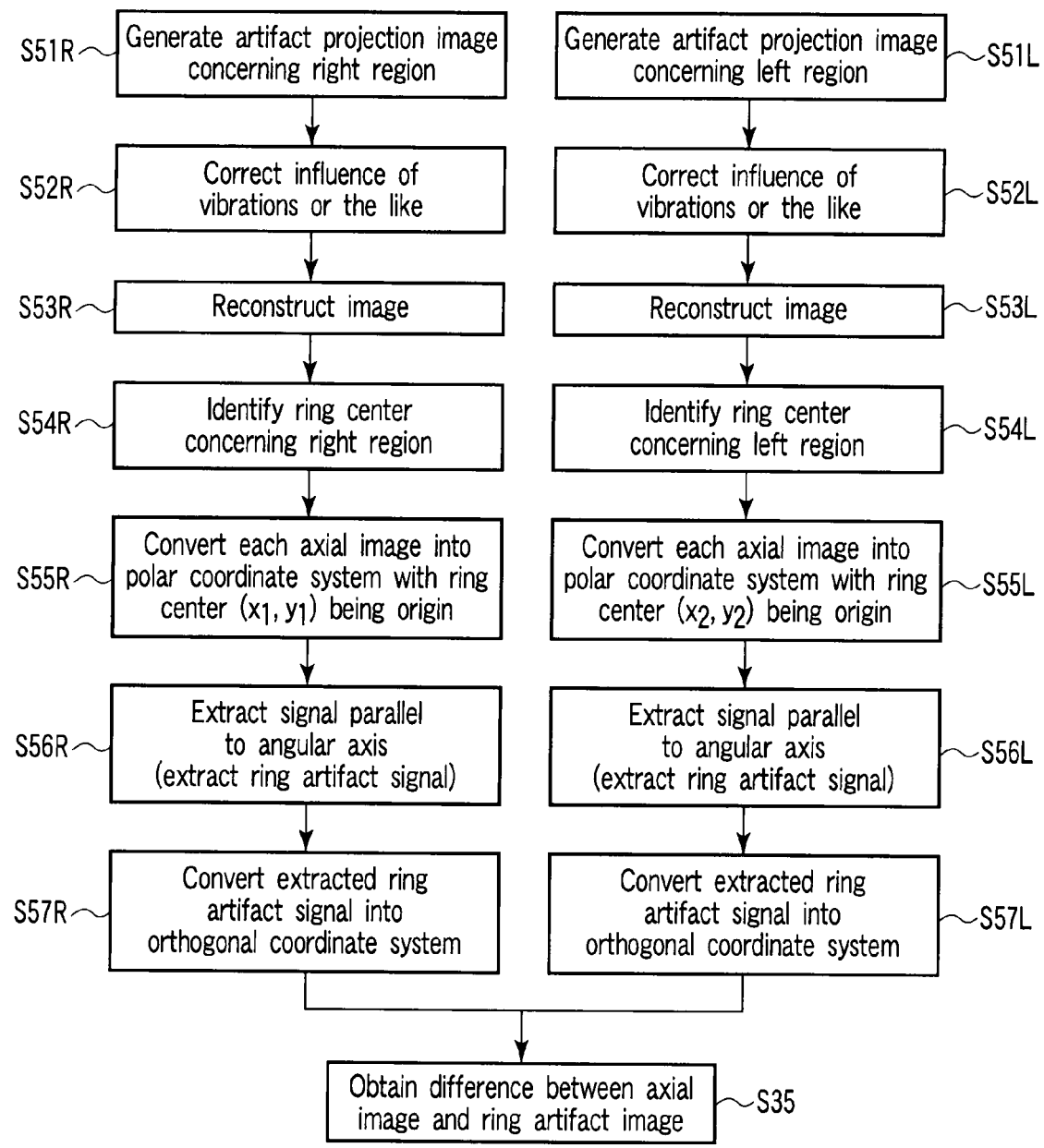
FIG. 11 is a flowchart showing the flow of a ring center identification process according to modification 3.
Figure 12:
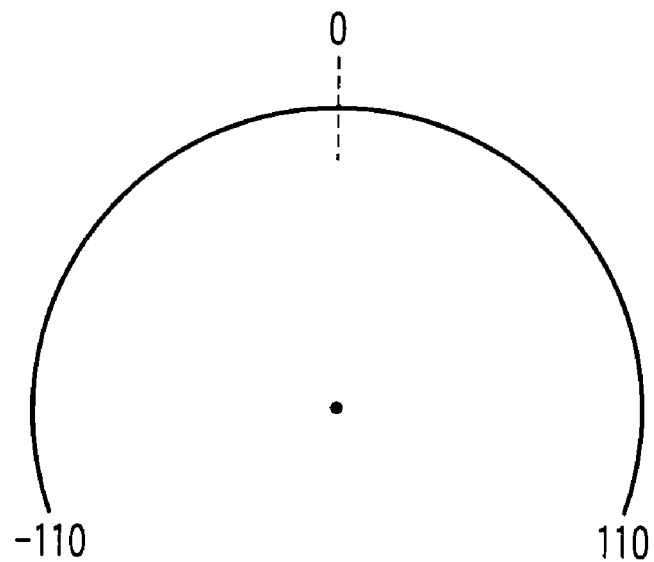
FIG. 12 is an explanatory diagram illustrating the ring center identification process according to modification 3.

FIG. 11 is a flowchart showing a procedure for ring center identification processing according to the modification 3. As shown in FIG. 12, a center identifying unit 9 divides the rotating region of the C-arm 23 (for example, −110 degrees to 110 degrees) into a right region (for example, −110 degrees to 0 degree) and a left region (for example, 0 degree to 110 degrees) with reference to the rotation origin, and generates an artifact projection image in which an artificial artifact is produced on the right side of the image central position in the projection direction belonging to the right region (step S51R). The center identifying unit 9 then executes the same processing as that in steps S2 to S4 in FIG. 2 to identify the ring central position ($x_1$, $y_1$) using the artifact reconstruction image belonging to the right region (steps S52R, S53R, and S54R).

On the other hand, the center identifying unit 9 generates an artifact projection image in which an artificial artifact is produced on the left side of the image central position in the projection direction belonging to the left region (step S51L), and executes the same processing as that in steps S2 to S4 in FIG. 2 to identify the ring central position ($x_2$, $y_2$) using the artifact reconstruction image belonging to the left region (steps S52L, S53L, and S54L).

Figure 13:
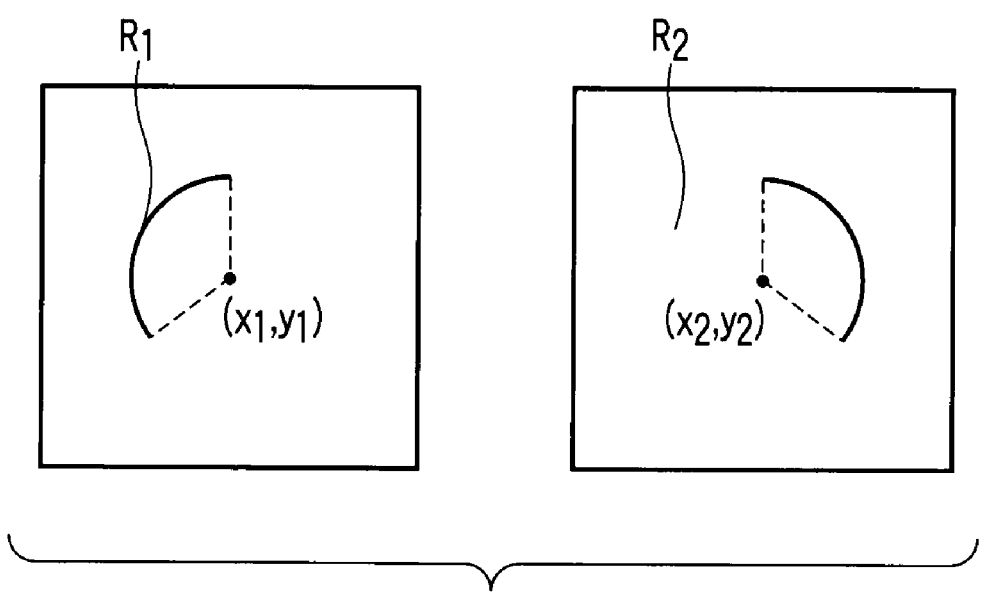
FIG. 13 is an explanatory diagram illustrating the ring center identification process according to modification 3.

That is, the center identifying unit 9 generates an axial image for each section by using each generated volume data. The axial image generated from the volume image corresponding to the right region includes an arcuated ring artifact R1 such as that shown in, for example, FIG. 13, whereas the axial image generated from the volume image corresponding to the left region includes an arcuated ring artifact R2 such as that shown in, for example, FIG. 13. The center identifying unit 9 identifies each of the ring central positions ($x_1$, $y_1$) and ($x_2$, $y_2$) by a predetermined method using the ring artifacts R1 and R2.

Next, The ring artifact correction unit 18 generates an axial image for each position of the section from the generated volume data obtained through the processes of, for example, steps S11 to S13, and converts the image coordinate system (the orthogonal coordinate system in this case) of each axial image into a polar coordinate system having the ring center ($x_1$, $y_1$) identified in advance as an origin (step S55R).

Each axial image generated by the volume data has an orthogonal coordinate system. In this orthogonal coordinate system, a ring artifact concentrically exists as its name implies. The ring artifact relating to the right region exists as data parallel to an angular axis in a range from −110 degrees to 0 degree (or 70 degrees to 180 degrees) of the polar coordinate system.

The ring artifact correction unit 18 extracts data which exists substantially parallel to the angular axis in a range from −110 degrees to 0 degree (or 70 degrees to 180 degrees) of the polar coordinate system (step S56R). The ring artifact correction unit 18 converts the extracted ring artifact into an orthogonal coordinate system to generate a ring artifact image (step S57R).

Similarly, the ring artifact correction unit 18 generates an axial image for each position of the section from the generated volume data obtained through the processes of, for example, steps S11 to S13, and converts the image coordinate system of each axial image into a polar coordinate system having the ring center ($x_2$, $y_2$) identified in advance as an origin (step S55L). The ring artifact relating to the left region exists as data parallel to an angular axis in a range from 0 degree to 110 degrees (or 180 degrees to 290 degrees) of the polar coordinate system.

The ring artifact correction unit 18 extracts data which exists substantially parallel to the angular axis in a range from 0 degree to 110 degrees (or 180 degrees to 290 degrees) of the polar coordinate system (step S56L). The ring artifact correction unit 18 converts the extracted ring artifact into an orthogonal coordinate system to generate a ring artifact image (step S57L).

Next, the ring artifact correction unit 18 removes the ring artifact from the volume data by subtracting the ring artifact image obtained in step S57R and the ring artifact image obtained in step S57L from each axial image (step S58).

According to the arrangement described above, the following effects can be obtained.

This X-ray diagnostic apparatus corrects the influences of the vibrations and the like of the rotational radiography system with respect to a projection image for each projection direction which contains an artificial artifact, and generates volume data containing only a ring artifact by the image reconstruction arrangement using the projection images. This apparatus determines a ring center by using this volume data and executes polar coordinate conversion of an actual projection image in ring artifact correction by using the ring center as an origin. In addition, the apparatus need not perform an identification of the positions of the rotation center by manual operation on reconstruction images, and can easily identify the coordinates of a ring center (rotation center) with fewer errors as compared with the prior art by using the identification of the positions of the rotation center by manual operation. Therefore, As a consequence, ring artifact correction with high accuracy can be easily implemented as compared with the prior art.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An identifying method of a central position of rotation of a rotational imaging system of an imaging apparatus which executes imaging while rotating, the method comprising:

obtaining a projection image which corresponds to each small region obtained by dividing a rotating region of the rotational imaging system with reference to a predetermined position and which contains an artificial artifact for each projection direction;

executing correction for removing an influence of a spatial positional shift due to a mechanical factor from the projection image;

reconstructing volume data containing a ring artifact due to the artificial artifact by using the corrected projection image; and identifying a ring center of the ring artifact as a position of a rotation center of the rotational imaging system by using the volume data.

2. A method according to claim 1, wherein the artificial artifact is generated parallel to a rotation axis of the rotational imaging system on the projection image.

3. A method according to claim 1, wherein
   in the reconstructing, the volume data is reconstructed as a plurality of partial volume data corresponding respectively to the small regions.

4. A method according to claim 1, wherein said plurality of rotating regions are determined on the basis of data associated with at least one of substantial center position, vibration, deflection, and backlash of the rotational imaging system.

5. A method according to claim 1, wherein
   in the reconstructing, the volume data is reconstructed as one volume data corresponding to the rotating region.

6. A method according to claim 5, wherein said plurality of rotating regions are determined on the basis of data associated with at least one of substantial center position, vibration, deflection, and backlash of the rotational imaging system.

7. A ring artifact correction method comprising:

obtaining a projection image which corresponds to each small region obtained by dividing a rotating region of the rotational imaging system with reference to a predetermined position and which contains an artificial artifact for each projection direction;

executing correction for removing an influence of a spatial positional shift due to a mechanical factor from the projection image;

reconstructing volume data containing a ring artifact due to the artificial artifact by using the corrected projection image;

identifying a ring center of the ring artifact as a position of a rotation center of the rotational imaging system by using the volume data; and correcting, using the ring center, a ring artifact occurring in a projection image acquired by using rotational imaging system for each projection direction.

8. A method according to claim 7, wherein the artificial artifact is generated parallel to a rotation axis of the rotational imaging system on the projection image.

9. A method according to claim 7, wherein
   in the reconstructing, the volume data is reconstructed as a plurality of partial volume data corresponding to the small regions.

10. A method according to claim 7, wherein said plurality of rotating regions are determined on the basis of data associated with at least one of substantial center position, vibration, deflection, and backlash of the rotational imaging system.

11. A method according to claim 7, wherein
    in the reconstructing, the volume data is reconstructed as one volume data corresponding to the rotating region.

12. A method according to claim 11, wherein said plurality of rotating regions are determined on the basis of data associated with at least one of substantial center position, vibration, deflection, and backlash of the rotational imaging system.

13. A method according to claim 7, wherein, when the ring center of the ring artifact is to be identified, the ring center is identified for each of small regions obtained by dividing the rotation region of the rotational imaging system with reference to a predetermined position, and when the artificial artifact is to be corrected, a plurality of ring artifact images corresponding respectively to the small regions are generated using the ring center of each of the small regions and differentiation process using each of the ring artifact images is carried out.

14. An apparatus for identifying a central position of rotation of a rotational imaging system of an imaging apparatus which executes imaging while rotating, the apparatus comprising:

an obtaining unit configured to obtain a projection image which corresponds to each small region obtained by dividing a rotating region of the rotational imaging system with reference to a predetermined position and which contains an artificial artifact for each projection direction;

a data processing unit which executes correction for removing an influence of a spatial positional shift due to a mechanical factor from the projection image;

a reconstructing unit configured to reconstruct volume data containing a ring artifact due to the artificial artifact by using the corrected projection image; and an identifying unit which identifies a ring center of the ring artifact as a position of a rotation center of the rotational imaging system by using the volume data.

15. An apparatus according to claim 14, wherein the artificial artifact is generated parallel to a rotation axis of the rotational imaging system on the projection image.

16. An apparatus according to claim 14, wherein in the reconstructing, the volume data is reconstructed as a plurality of partial volume data corresponding to the small regions.

17. An apparatus according to claim 14, wherein said plurality of rotating regions are determined on the basis of data associated with at least one of substantial center position, vibration, deflection, and backlash of the rotational imaging system.

18. An apparatus according to claim 14, wherein in the reconstructing, the volume data is reconstructed as one volume data corresponding to the rotating region.

19. An apparatus according to claim 18, wherein said plurality of rotating regions are determined on the basis of data associated with at least one of substantial center position, vibration, deflection, and backlash of the rotational imaging system.

20. An X-ray diagnostic apparatus comprising:

an obtaining unit configured to obtain a projection image which corresponds to each small region obtained by dividing a rotating region of the rotational imaging system with reference to a predetermined position and which contains an artificial artifact for each projection direction;

a data processing unit which executes correction for removing an influence of a spatial positional shift due to a mechanical factor from the projection image;

a reconstructing unit configured to reconstruct volume data containing a ring artifact due to the artificial artifact by using the corrected projection image;

an identifying unit which identifies a ring center of the ring artifact as a position of a rotation center of the rotational imaging system by using the volume data; and a correction unit which corrects, using the ring center, a ring artifact occurring in a projection image acquired by using rotational imaging system for each projection direction.

21. An apparatus according to claim 20, wherein the artificial artifact is generated parallel to a rotation axis of the rotational imaging system on the projection image.

22. An apparatus according to claim 20, wherein in the reconstructing, the volume data is reconstructed as a plurality of partial volume data corresponding to the small regions.

23. An apparatus according to claim 20, wherein in the reconstructing, the volume data is reconstructed as one volume data corresponding to the rotating region.

24. The X-ray diagnostic apparatus according to claim 20, wherein, the ring center identification unit identifies a ring center for each of small regions obtained by dividing the rotation region of the rotational imaging system with reference to a predetermined position, and the correction unit generates a plurality of ring artifact images corresponding respectively to the small regions using the ring center of each of the small regions and executes a differentiation process using each of the ring artifact images.

25. An apparatus according to claim 22, wherein said plurality of rotating regions are determined on the basis of data associated with at least one of substantial center position, vibration, deflection, and backlash of the rotational imaging system.

26. An apparatus according to claim 23, wherein said plurality of rotating regions are determined on the basis of data associated with at least one of substantial center position, vibration, deflection, and backlash of the rotational imaging system.

27. A non-transitory computer readable recording medium configured to store computer executable instructions for an identifying method of a central position of rotation of a rotational imaging system of an imaging apparatus which executes imaging while rotating on a computer system enabling the computer system to perform:

obtaining a projection image which corresponds to each small region obtained by dividing a rotating region of the rotational imaging system with reference to a predetermined position and which contains an artificial artifact for each projection direction;

executing correction for removing an influence of a spatial positional shift due to a mechanical factor from the projection images;

reconstructing volume data containing a ring artifact due to the artificial artifact by using the corrected projection images; and identifying a ring center of the ring artifact as a position of a rotation center of the rotational imaging system by using the volume data.

28. A non-transitory computer readable recording medium configured to store computer executable instructions for executing ring artifact correction on a computer system enabling the computer system to perform:

obtaining a projection image which corresponds to each small region obtained by dividing a rotating region of the rotational imaging system with reference to a predetermined position and which contains an artificial artifact for each projection direction;

executing correction for removing an influence of a spatial positional shift due to a mechanical factor from the projection image;

reconstructing volume data containing a ring artifact due to the artificial artifact direction by using the corrected projection image;

identifying a ring center of the ring artifact as a position of a rotation center of the rotational imaging system by using the volume data; and correcting, using the ring center, a ring artifact occurring in a projection image acquired by using rotational imaging system for each projection direction.

* * * * *